United States Patent [19]
Billmers

[11] Patent Number: 5,350,354
[45] Date of Patent: Sep. 27, 1994

[54] WATER-DISPOSABLE TAMPON APPLICATORS AND BIODEGRADABLE COMPOSITION FOR USE THEREIN

[75] Inventor: Robert L. Billmers, Stockton, N.J.

[73] Assignee: National Starch and Chemical Investment Holding Corporation, Wilmington, Del.

[21] Appl. No.: 802,786

[22] Filed: Dec. 6, 1991

Related U.S. Application Data

[63] Continuation-in-part of Ser. No. 457,658, Dec. 27, 1989.

[51] Int. Cl.$^5$ .............................. A61F 13/70
[52] U.S. Cl. ...................... 604/11; 604/12; 604/15
[58] Field of Search ............. 536/102; 604/11-18

[56] References Cited

U.S. PATENT DOCUMENTS

| | | | |
|---|---|---|---|
| 3,015,332 | 1/1962 | Brecht | 604/15 |
| 3,137,592 | 6/1964 | Protzman et al. | 127/32 |
| 3,336,429 | 8/1967 | Carevic | 264/186 |
| 3,419,005 | 12/1968 | Lewing | 604/11 |
| 3,429,312 | 2/1969 | Stump | 604/15 |
| 3,882,196 | 5/1975 | Hanke | 260/895 |
| 3,882,869 | 5/1975 | Hanke | 128/263 |
| 3,891,624 | 6/1975 | Boonstra et al. | 260/233.3 R |
| 3,954,104 | 5/1976 | Kraskin et al. | 128/263 |
| 4,099,976 | 7/1978 | Kraskin et al. | 106/15 R |
| 4,673,438 | 6/1987 | Wittwer et al. | 106/126 |
| 4,863,655 | 9/1989 | Lacourse et al. | 264/53 |
| 5,032,683 | 7/1991 | Dragners et al. | 536/102 |
| 5,035,930 | 7/1991 | Lacourse et al. | 428/35.6 |
| 5,043,196 | 8/1991 | Lacourse et al. | 428/35.6 |

FOREIGN PATENT DOCUMENTS

| | | | |
|---|---|---|---|
| 0304401 | 2/1989 | European Pat. Off. | 604/11 |
| 0965349 | 7/1964 | United Kingdom | 604/11 |
| 2202750 | 10/1988 | United Kingdom | 604/11 |

*Primary Examiner*—Randall L. Green
*Assistant Examiner*—Rob Clarke
*Attorney, Agent, or Firm*—Eugene Zagarella, Jr.

[57] ABSTRACT

This invention provides biodegradable tampon applicators adapted for disposal in water-base toilet systems. This invention also provides plasticized starch compositions for use in fabrication of tampon applicators and methods for fabrication thereof.

14 Claims, 1 Drawing Sheet

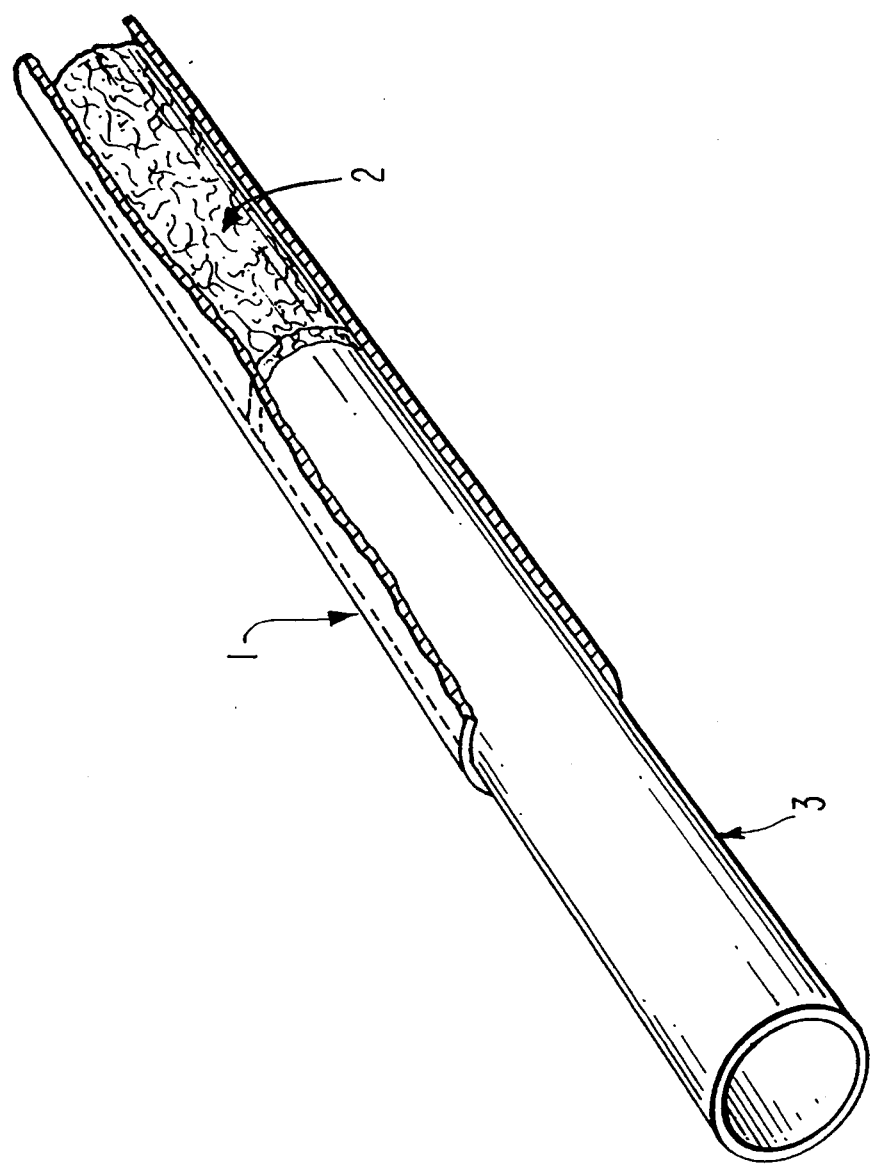

WATER-DISPOSABLE TAMPON APPLICATORS AND BIODEGRADABLE COMPOSITION FOR USE THEREIN

This application is a continuation-in-part of application Ser. No. 07/457,658 filed Dec. 27, 1989.

This invention relates to biodegradable tampon applicators adapted for disposal in water-base toilet systems. This invention also relates to plasticized starch compositions and the fabrication of tampon applicators from such compositions.

BACKGROUND OF THE INVENTION

Tampon insertion devices ("applicators") of a telescoping tube type are often disposed of by dropping them into a toilet. Thus, it is desirable that applicators be fabricated from a composition which rapidly softens and disperses in water, yet retains its form during use and is shelf-stable under ambient conditions. Such a composition avoids the danger of stoppages of toilet and sewer systems. Biodegradability is also a desirable characteristic.

Compositions suggested for use in such applicators include water soluble polymers, synthetic (e.g., polyoxyethylene polymers) and natural (e.g., cellulose derivatives), and fillers such as talc, clay, hydrated silicates and starch. See, e.g., U.S. Pat. Nos. 3,882,869, issued May 13, 1975 to Hanks; 3,954,104, issued May 4, 1976 to Kraskin, et al.; and 4,099,976, issued Jul. 11, 1978 to Kraskin, et al. These compositions disadvantageously require the presence of non-water-dispersible fillers to reduce cost and/or cellulose derivatives to impart thermoplastic characteristics to the composition.

Starch and other polysaccharides have been suggested for use in biodegradable packaging and container materials. Starches typically are employed as an adjunct to other, conventional packaging materials to improve biodegradability. However, in a few cases starches have been employed as the primary component of containers (i.e., U.S. Pat. No. 4,673,438, issued Jun. 16, 1987 to Wittwer, et al.), and packaging materials and products (i.e., U.S. Pat. No. 4,863,655, issued Sep. 5, 1989 to Lacourse, et al.; U.S. Pat. No. 5,035,930, issued Jul. 30, 1991 to Lacourse, et al.; and U.S. Pat. No. 5,043,196 issued Aug. 27, 1991 to Lacourse, et al., all commonly assigned herewith).

The biodegradable, starch-containing packaging and container materials known in the art are typically prepared to be water-resistant, rather than water-dispersible. Thus, there remains a need for other, biodegradable compositions for use in fabricating toilet-disposable tampon applicators.

SUMMARY OF THE INVENTION

This invention provides a water-dispersible, toilet-disposable, biodegradable applicator for tampons comprising a self-supporting, open-ended tube having a composition of 45 to 90%, by weight, starch, 5 to 40%, by weight, plasticizer and 5 to 15%, by weight, water. The applicator may further comprise a substantially rigid plunger or inner tube movably received within the tube and adapted to expel a tampon from within the outer open-ended tube. The applicator typically has a water content of less than 15%, preferably less than 10%, by weight, and a water activity of less than 0.80, and is resistant to microbial growth up to 30° C. and from 30–80% relative humidity. The applicator may further comprise at least one component selected from the group consisting of antimicrobial agents, lubricants, fillers (e.g., dextrin), colorants, fragrances, and the like.

Also provided are biodegradable, toilet-disposable, thermoplastic compositions, comprising 30 to 70%, by weight, starch, 10 to 40%, by weight, plasticizer and 20 to 60%, by weight, water, and methods for fabricating tampon applicators by molding, casting or extrusion of these compositions.

BRIEF DESCRIPTION OF THE DRAWING

FIG. 1 is a perspective view of one embodiment of a tampon applicator of this invention showing a tampon with parts broken away. The embodiment shown in FIG. 1 comprises outer tube 1 made of the composition of the invention, having tampon 2 movably received within one end thereof and plunger 3 movably received within the other end thereof. The tampon containing end of the applicator is inserted into the body cavity and the tampon is expelled therefrom by the pressure of the plunger. This plunger may be made of the composition of the invention.

DESCRIPTION OF THE PREFERRED EMBODIMENTS

Starches which may be used herein may be derived from any source, including corn, potato, sweet potato, wheat, rice, sago, tapioca, waxy maize, sorghum, high amylose corn, or the like. Starch flours also may be used. Also useful herein are the conversion products derived from any of these starches including, for example, dextrins prepared by the hydrolytic action of acid and/or heat; oxidized starches prepared by treatment with oxidants such as sodium hypochlorite; fluidity or thin-boiling starches prepared by enzyme conversion or mild acid hydrolysis; and derivatized (e.g., cationic, anionic, amphoteric, and non-ionic) starches and crosslinked starches. Prior to formulating the compositions useful herein, the starch may be in a granular form or a gelatinized form (i.e., cooked, non-granular starch).

Methods for preparing modified starches are well known to those skilled in the art and are discussed in the literature. See, for example, R. L. Whistler, *Methods in Carbohydrate Chemistry*, Vol. IV, 1964, pp. 279–331; R. L. Whistler, et al., *Starch-Chemistry and Technology*, Vol. II, 1967, pp. 293–430; R. L. Davidson, *Handbook of Water-Soluble Gums and Resins*, 1980, Chapter 22, directed to starch; and O. Wurzburg, *Modified Starches: Properties and Uses*, CRC Press, 1986.

The starch may be cooked prior to derivatization, or subsequent to derivatization. The starch must be cooked and hydrated (to gelatinization) and be in a dispersed state for use in the compositions herein. Any conventional cooking procedure may be used, such as jet-cooking, or cooking a slurry containing the water-soluble or water-swellable starch derivatives in a boiling water bath for 20 minutes and blowing in steam to heat the slurry to about 93° C. (200° F.).

Converted corn starch, derivatized by reaction with a $C_2$–$C_6$ alkylene oxide, is preferred herein. Propylene oxide is preferred. Propylene oxide treatment increases the water-dispersibility of the starch, permits use of the starch derivative as food grade material and reduces the amount of plasticizer needed to fabricate articles with acceptable tensile strength.

Also preferred is a light crosslinking treatment of the gelatinized starch in a dispersed state for building starch film strength and permitting fabrication of a substantially rigid article. Too much crosslinking tends to limit water dispersibility. Preferred results are achieved by lightly crosslinking dispersed starch with, e.g., glyoxal,

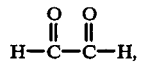

at a treatment level up to 1%, by weight of starch, preferably up to a maximum treatment level of 0.5%. Very high strength starch films are to be avoided so as to retain water-dispersibility.

Likewise, as the percent amylose increases, starch film strength increases and water-dispersibility decreases. Therefore, unmodified high amylose starches (i.e., starches containing more than 40% amylose) are typically avoided in compositions used for fabricating tampon applicators. Derivatized and/or converted high amylose starches are more water-dispersible than their unmodified counterparts and are suitable for use in tampon applicators. Further, even unmodified high amylose starch may be used if blended with an adjunct, such as dextrin or a highly converted fluidity starch, which absorbs water or otherwise improves water-dispersibility of the high amylose starches.

Dextrins and fluidity starches also may be selected to control the viscosity of the starch composition as needed for manufacture of the applicators.

Plasticizers employed herein typically include sorbitol, polyalkylene glycols such as polyethylene glycol, glycerol, polyethyleneamine, alkylene glycols such as ethylene glycol, tetra-alkyl ammonium salts, tri-alkyl citrates or mono-, di- or triacetates of glycerol, sugars such as fructose, corn syrup or a combination thereof. Other plasticizers known in the art also may be employed. For tampon applicators useful plasticizers are limited to non-toxic, water-dispersible and non-volatile materials.

Prior to fabrication of the tampon applicators, compositions useful therein comprise 30 to 70% starch, 10 to 40% plasticizer and 20 to 60% water, depending upon the method of fabrication to be employed. Extrusion processing requires less water (20–40%) than casting (30–60%), more starch (35-70% versus 30–50%) and less plasticizer (10–40% versus 20–40%).

Optionally, these compositions may further comprise lubricants, fillers, colorants or opacifying agents, anti-microbial agents, fragrances and other additional components for use in tampon applicators.

Lubricants may be used in the compositions to facilitate the manufacture of articles therefrom. The preferred lubricants are lauryl thiodipropionate, glycerol monostearate, and various polyalkylene glycols, such as polyethylene glycol, polypropylene glycol, and the like, sold by Union Carbide Corporation under the tradename CARBOWAX.

Although these starch-containing compositions provide milky, opaque articles, additional opacity, color or whiteness may be achieved by employing titanium dioxide or other suitable opacifying material or colorant.

Because biodegradable starch-containing compositions are, by definition, susceptible to microbial attack under certain conditions, the control of microbial attack is an important element in formulating a shelf-stable composition. In a preferred embodiment, the water content and the water activity of the tampon applicators prepared from the starch compositions are controlled so as to eliminate microbial attack. Water activity is the ratio of the vapor pressure of the tampon applicators to the vapor pressure of water at the same temperature. The water activity at which microbial growth is eliminated varies depending primarily upon water content of the applicator, temperature, ambient relative humidity, surface area and shape of the applicator, presence of salts and presence of other materials which affect microbial growth.

For tampon applicators prepared from starch compositions disclosed herein, a water activity of less than 0.80, preferably less than 0.70, is preferred for shelf stability. A water content of less than 15%, preferably less than 10%, is also preferred. As the water content is decreased, higher water activities may be acceptable. Likewise, as water activity is decreased, water content may be increased.

Because water activity changes as ambient temperature and relative humidity changes, storage of tampon applicators at less than 30° C. and less than 80% relative humidity is preferred. In the alternative, an outer package having a moisture barrier may be employed.

In another preferred embodiment, anti-microbial agents may be added to the starch composition. Such agents are known in the art and are exemplified by sorbic acid and its alkali salts which may be used at from about 0.05% to 3%, by weight of the starch composition, preferably at 0.1% to 0.3%.

As will be readily determined by the practitioner, other anti-microbial agents and other preferred ranges of water activity, water content and storage conditions may be employed.

The tampon applicators of the invention generally comprise a self-supporting open ended tube which is water-dispersible, toilet-disposable and biodegradable. This applicator tube which holds a tampon may be used alone or further comprise a plunger or inner tube as illustrated in FIG. 1. This plunger or inner tube is normally positioned or movably received within one end of the outer open ended tube and is adapted to expel a tampon from the other end of the open ended tube by the movement and pressure of said plunger or inner tube. This plunger or inner tube is not always toilet disposed and in some instances it is reused in other tube containing tampon applicators. Therefore, the plunger or inner tube may be made of any material that makes it substantially rigid. Preferably, the plunger or inner tube will be made of the same material as the tampon holding applicator tube making it water-dispersible, toilet-disposable and biodegradable.

The tampon applicators herein may be fabricated by any method known in the art of forming or shaping plastic materials. For example, an extrusion process, either alone or in combination with other forming or molding operations, may be used. By varying the size and configuration of the die opening of the extruder, different forms, such as tubes of varying thickness and widths, sheets and other shapes may be fabricated. The starch composition leaving the extruder is typically hot and malleable and may be thermomolded. Methods for extruding starches are well known in the art. See, for example, R.Chinnaswamy and M. A. Hanna, *J. Fd. Sci.,* 53:3, pp. 834–838 (1988); and C. Mercier, P. Linko, J. M. Harper, *Extrusion Cooking,* The American Association of Cereal Chemists, Inc. St. Paul, Minn., 1989. Other methods, including injection molding, blow molding, extrusion/blow molding, stamping and casting, and combinations thereof, may be employed herein.

Whatever method is chosen, it is critical that the finished tampon applicator have a substantially rigid shape and retain some tensile strength and plasticity along with a water-dispersible, biodegradable character.

In the examples which follow, all parts and percentages are given by weight and all temperatures are in degrees Celsius unless otherwise noted. Reagent percentages are based on dry starch.

EXAMPLE 1

This example illustrates the preparation of the starch-containing compositions and tampon applicators of this invention.

The compositions set forth in Table 1 were prepared by the methods described below and in the footnotes to Table 1.

The starch, sorbitol solution, water and dextrin, where applicable, were blended and cooked in a boiling water bath for 20 minutes. In the alternative, the composition was cooked at 149° C. (300° F.) to gelatinization in a jet-cooker.

Where applicable, the compositions were treated after cooking with glyoxal to lightly crosslink the dispersed starch.

(Thwing-Albert Instrument Company, Philadelphia, Pa.). Results are shown in Table I.

Crosslinking improved the load strength of the films in a linear manner. Crosslinking caused an initial increase in tensile strength followed by a decrease as more glyoxal was employed. Thus, an optimum level of crosslinking (at about 0.5%, by starch weight, maximum) was identified.

As a filler, dextrin had a beneficial effect on film strength.

After curing the films for 24 hours at 50-70% relative humidity, the films were rolled into tubes on a 1.0 inch lucite rod coated with a thin film of mineral oil. This assembly was rolled between weighted plates to fuse the film and form rigid tubes.

The tubes were removed from the rod and stored at ambient temperature and humidity for more than three months. They maintained their shape throughout the storage period. No microbial growth was observed on the tubes. The water content of the stored tubes was 8%, by weight.

When placed in water, the tubes softened quickly, lost their shape within 10-120 seconds (depending on tube thickness), broke-up, and dissolved within minutes.

This invention has been described in terms of specific

TABLE 1

Characteristics of Biodegradable Placticized Starch Compositions[a]

| Wet Film[d] Thickness (in.) | Starch (g) | Water (g) | Dextrin[b] (g) | Glyoxal[c] (ml) | Load (g) | Elongation (%) | TEA[e] |
|---|---|---|---|---|---|---|---|
| 0.006 | 22 | 15 | 17 | — | 982.0 | 35.00 | 294.00 |
| 0.006 | 22 | 15 | 17 | 0.5 | 717.5 | 54.30 | 339.20 |
| 0.006 | 22 | 15 | 17 | 1.0 | 631.0 | 69.40 | 359.80 |
| 0.006 | 22 | 15 | 17 | 5.0 | 694.0 | 68.00 | 386.00 |
| 0.006 | 22 | 15 | 17 | 10.0 | 1032.0 | 53.00 | 482.00 |
| 0.01 | 22 | 15 | 17 | — | 976.0 | 48.00 | 412.00 |
| 0.01 | 22 | 15 | 17 | 0.5 | 717.5 | 54.30 | 339.20 |
| 0.01 | 22 | 15 | 17 | 1.0 | 796.0 | 46.30 | 319.20 |
| 0.01 | 22 | 15 | 17 | 5.0 | 803.0 | 71.00 | 454.15 |
| 0.01 | 22 | 15 | 17 | 10.0 | 660.0 | 51.00 | 272.00 |
| 0.01 | 17 | 20 | 17 | — | 10.8 | 33.87 | 3.10 |
| 0.01 | 22 | 20 | 12 | — | 24.4 | 35.00 | 7.70 |
| 0.02 | 22 | 15 | 17 | — | 1775.0 | 39.40 | 601.0 |
| 0.02 | 22 | 15 | 17 | 0.5 | 1476.0 | 44.00 | 562.8 |
| 0.02 | 22 | 15 | 17 | 1.0 | 1337.0 | 48.34 | 559.0 |
| 0.02 | 22 | 15 | 17 | 5.0 | 1367.0 | 166.00 | 1517.0 |
| 0.02 | 22 | 15 | 17 | 10.0 | 1979.0 | 35.06 | — |
| 0.02 | 17 | 20 | 17 | — | 14.0 | 40.00 | 5.1 |
| 0.02 | 22 | 20 | 12 | — | 36.6 | 27.80 | 8.9 |

[a]All compositions contained 41 g of a 40.3% solution of sorbitol in water.
[b]All compositions employed an acid-converted, fluidity corn starch, having a Water Fluidity of 67 (Flogel G, National Starch and Chemical Corporation).
[c]After the starch had been cooked, glyoxal, in amounts indicated above, was added to the composition to lightly crosslink the starch and increase resultant starch film strength.
[d]The average moisture content of the films after drying ranged from 8 to 12%.
[e]Total Engergy Absorbed.

Plasticized starch films were prepared from the compositions of Table 1 by coating the cooked and cooled composition onto a teflon-coated plate employing a Bird Applicator (MCD Industries, Medford, Mass.) to give a 0.006, 0.01 or 0.02 inch thick wet film.

The films were tested for load (the grams of force required to break a 1 inch wide by 4 inch long strip of film), elongation (the distance the 1×4 inch strip stretches before breaking, expressed as a % of 4) inches and the Total Energy Absorbed (TEA). These tensile strength measurements were made in accordance with TAPPI T496 method ("Tensile Breaking Properties of Paper and Paperboard [Using Constant Rate of elongation Apparatus], TAPPI T494, 1982). The apparatus used for the tests was a Model II Intellect Machine embodiments set forth in detail, but it should be understood that these are by way of illustration only and that the invention is not necessarily limited thereto. Modifications and variations may be resorted to without departing from the spirit of this invention, as those skilled in the art will readily understand. Accordingly, such variations and modifications of the disclosed invention are considered to be within the scope of this invention and the following claims.

What is claimed is:

1. A water-dispersible, toilet-disposable, biodegradable applicator for tampons comprising a self-supporting, open-ended tube having a composition consisting essentially of 45 to 90%, by weight, starch, 5 to 40%, by weight, plasticizer and 5 to 15%; by weight water and wherein the starch contains a) 40% or less of amylose or b) more than 40% by weight amylose modified with up to 20%, by weight propylene oxide, and is dispersed by being gelatinized prior to formation of the applicator to provide water-dispersibility to the applicator and a substantially rigid plunger or inner tube movably received within said open-ended tube and adapted to expel a tampon therefrom.

2. The applicator of claim 1 further comprising dextrin.

3. The applicator of claim 1, wherein the applicator has a water content of less than 15%, by weight, and a water activity of less than 0.80, and is resistant to microbial growth at less than 30° C. and less than 80% relative humidity.

4. The applicator of claim 1, wherein the starch contains 40% or less amylose and is derivatized by reaction with up to 20%, by weight propylene oxide.

5. The applicator of claim 1, wherein the starch is dispersed in water, gelatinized and crosslinked.

6. The applicator of claim 1, wherein the starch is crosslinked by reaction with up to 0.5% glyoxal.

7. The applicator of claim 1, further comprising at least one component selected from the group consisting of antimicrobial agents, lubricants, fillers, colorants, and fragrances.

8. The applicator of claim 7, wherein the filler is dextrin.

9. The applicator of claim 1, wherein the plasticizer is sorbitol, polyalkylene glycol, glycerol, polyethyleneamine, alkylene glycol, tetra-alkyl ammonium salts, tri-alkyl citrates or mono-, di- or triacetates of glycerol, sugar, corn-oil or a combination thereof.

10. The applicator of claim 9 wherein the applicator has a water content of less than 15%, by weight, and a water activity of less than 0.80, and is resistant to microbial growth at less than 30° C. and less than 80% relative humidity.

11. The applicator of claim 2 wherein the applicator has a water content of less than 15%, by weight, and a water activity of less than 0.80, and is resistant to microbial growth at less than 30° C. and less than 80% relative humidity.

12. The applicator of claim 11, wherein the starch contains 40% or less amylose and is derivatized with up to 20%, by weight, propylene oxide.

13. The applicator of claim 12, wherein the plasticizer is sorbitol, polyalkylene glycol, glycerol, polyethyleneamine, alkylene glycol, tetra-alkyl ammonium salts, tri-alkyl citrates or mono-, di-, or triacetates of glycerol, sugar, corn oil, or a combination thereof.

14. The applicator of claim 13 wherein the applicator has a water content of less than 15%, by weight, and a water activity of less than 0.80, and is resistant to microbial growth at less than 30° C. and less than 80% relative humidity.

* * * * *